United States Patent
Sela et al.

(10) Patent No.: US 10,675,269 B2
(45) Date of Patent: Jun. 9, 2020

(54) COMPOSITIONS COMPRISING MELATONIN

(71) Applicant: TRINUTRA LTD., Nes Ziona (IL)

(72) Inventors: Yoram Sela, Ra'anana (IL); Mor Zeilkha, Ramat Gan (IL); Itschak Lamensdorf, Modi'in (IL)

(73) Assignee: TRINUTRA LTD., Nes Ziona (IL)

( * ) Notice: Subject to any disclaimer, the term of this patent is extended or adjusted under 35 U.S.C. 154(b) by 0 days.

(21) Appl. No.: 16/070,925

(22) PCT Filed: Jan. 17, 2017

(86) PCT No.: PCT/IL2017/050060
§ 371 (c)(1),
(2) Date: Jul. 18, 2018

(87) PCT Pub. No.: WO2017/125919
PCT Pub. Date: Jul. 27, 2017

(65) Prior Publication Data
US 2019/0029999 A1    Jan. 31, 2019

Related U.S. Application Data

(60) Provisional application No. 62/279,936, filed on Jan. 18, 2016.

(51) Int. Cl.
| | | |
|---|---|---|
| A61K 36/00 | (2006.01) | |
| A61K 31/4045 | (2006.01) | |
| A61K 31/185 | (2006.01) | |
| A61K 36/185 | (2006.01) | |
| A61K 31/191 | (2006.01) | |
| A61P 25/20 | (2006.01) | |
| A61P 25/22 | (2006.01) | |
| A61P 29/00 | (2006.01) | |
| A61K 9/00 | (2006.01) | |
| A61K 31/192 | (2006.01) | |
| A61K 36/84 | (2006.01) | |

(52) U.S. Cl.
CPC ......... *A61K 31/4045* (2013.01); *A61K 9/006* (2013.01); *A61K 31/185* (2013.01); *A61K 31/191* (2013.01); *A61K 36/185* (2013.01); *A61P 25/20* (2018.01); *A61P 25/22* (2018.01); *A61P 29/00* (2018.01); *A61K 31/192* (2013.01); *A61K 36/84* (2013.01); *A61K 2300/00* (2013.01)

(58) Field of Classification Search
None
See application file for complete search history.

(56) References Cited

U.S. PATENT DOCUMENTS

| | | |
|---|---|---|
| 6,277,396 B1 | 8/2001 | Dente |
| 6,383,526 B1 | 5/2002 | Andrews et al. |
| 2002/0182196 A1 | 12/2002 | McCleary |
| 2004/0001817 A1 | 1/2004 | Giampapa |
| 2006/0264497 A1 | 11/2006 | Zeligs |
| 2009/0068255 A1* | 3/2009 | Yu .......... A61K 8/0212 424/450 |
| 2012/0294952 A1 | 11/2012 | Zarbock et al. |
| 2013/0004599 A1 | 1/2013 | Schwartz |
| 2013/0012824 A1 | 1/2013 | Vanney et al. |
| 2013/0315983 A1 | 11/2013 | Einbond et al. |
| 2015/0071993 A1 | 3/2015 | Patel et al. |

FOREIGN PATENT DOCUMENTS

| | | |
|---|---|---|
| WO | 01/26646 | 4/2001 |
| WO | 2008/036979 | 3/2008 |

OTHER PUBLICATIONS

International Search Report for PCT/IL2017/050060, dated Jun. 19, 2017, 7 pages.
Written Opinion of the ISA for PCT/IL2017/050060, dated Jun. 19, 2017, 9 pages.
Kirubakaran Shanmugam et al: "Plant-derived polyphenols attenuate lipopolysaccharide-induced nitric oxide and tumour necrosis factor production in murine microglia and macrophages", Mol. Nutr. Food Res, vol. 52, Jan. 1, 2008 (Jan. 1, 2008), pp. 427-438.
Roberta Foresti et al: "Small molecule activators of the Nrf2-HO-1 antioxidant axis modulate heme metabolism and inflammation in BV2 microglia cells", Pharmacological Research., vol. 76, dated Oct. 1, 2013 (Oct. 1, 2013), GB, pp. 917-919, XP055230780.
Jacobo-Herrera et al: Nf-[kappa]B Modulators, Jan. 1, 2006 (Jan. 1, 2006), pp. 917-919.
Clark, I. A. and Vissel, B. Inflammation-sleep interface in brain disease: TNF, insulin, orexin (2014).

* cited by examiner

*Primary Examiner* — Qiuwen Mi
(74) *Attorney, Agent, or Firm* — Nixon & Vanderhye P.C.

(57) ABSTRACT

The present invention provides a composition comprising a synergistic combination of melatonin, valerenic acid and carnosic acid. The composition may be used in the treatment and prevention of several different disorders including inflammatory conditions, sleep disorders and anxiety. The invention also relates to several dosage forms which are suitable for the delivery of the claimed composition to subjects in need of treatment therewith.

13 Claims, 3 Drawing Sheets

COMPOSITIONS COMPRISING MELATONIN

This application is the U.S. national phase of International Application No. PCT/IL2017/050060 filed 17 Jan. 2017, which designated the U.S. and claims the benefit of U.S. Provisional Application No. 62/279,936 filed 18 Jan. 2016, the entire contents of each of which are hereby incorporated by reference.

FIELD OF THE INVENTION

The present invention relates to novel compositions that comprise melatonin, and which may further comprise one or more additional active ingredients that synergistically enhance the biological activity of said compositions.

BACKGROUND OF THE INVENTION

Melatonin (N-acetyl-5-methoxytryptamine) is a naturally occurring substance that is found in animals, plants, fungi and bacteria. In humans and other mammals, melatonin is produced by the pineal gland and acts as a neurohormone, playing a key role in the maintenance of circadian rhythms. As such, it has a significant influence on many physiological functions including sleep. In this regard, it has been found that melatonin may be used in order to regularize sleep and to treat certain sleep disorders, notably insomnia.

Various clinical studies of the use of melatonin in the treatment of insomnia have been performed, and the results of some of these studies indicate that prolonged-release melatonin may indeed be effective in improving sleep latency, sleep quality and daytime alertness in adults. Other studies have also shown that melatonin administration may provide an effective treatment sleep-wake cycle disorders associated with neurodevelopmental disorders in children.

In addition to its effects on sleep, a number of additional and different health benefits have been associated with melatonin. For example, melatonin has been found, in a number of well documented studies, to have a variety of effects on inflammatory and immune processes (both as an activator and an inhibitor of these processes). In this regard, it has been found that melatonin controls the production of many different inflammatory mediators, including but not limited to leukotrienes and cytokines. In addition to specific actions on various mediator systems, melatonin may also modulate ongoing inflammatory processes by virtue of its potent antioxidant effects.

Several studies have indicated that sleep patterns are altered during inflammatory disease, and to some degree may be considered as markers of the presence and severity of the inflammatory process.

Furthermore, several different inflammatory mediator systems have been implicated in causing changes in sleep patterns. It may therefore be concluded that there is a type of inflammation-sleep interface (Clark, I. A. and Vissel, B. (2014) J. Neuroinflammation 11: 51 *Inflammation-sleep interface in brain disease: TNF, insulin, orexin*), and thus agents which modulate various aspects of the inflammatory process may also be capable of influencing sleep patterns and behaviour.

A very large number of different chemical mediators have been shown to be involved in the development and control of the inflammatory process. Recent studies by a number of different laboratories have implicated nitric oxide (NO) as an important modulator of a variety of acute and chronic inflammatory disorders, including various types of arthritis, gastro-intestinal diseases, inflammatory conditions of the central nervous system and certain forms of asthma. Consequently, it has been proposed that inhibition of NO production could provide a useful therapeutic mechanism for the treatment and/or management of these inflammatory disorders.

Melatonin may also play a role in several other physiological and pathological processes, and it has been suggested that adequate levels of this hormone may play a role in protecting against cardiovascular disease, various different cancers and several different degenerative conditions affecting the central nervous system.

Several plant-derived preparations have also been used to treat insomnia and other sleep disorders, with various degrees of success. These plant-derived treatments include extracts, tinctures, teas, oils or whole-plant material from inter alia the following species: valerian (*Valeriana officinalis*), passiflora (*Passiflora incarnata*), chamomile (*Anthemis nobilis*), Hops (*Humulus lupulus*), lavender (*Lavandula officinalis*), wild lettuce (*Lactuca virosa*), california poppy (*Eschsholzia californica*), Kava kava (*Piper methysticum*) and St. John's wort (*Hypericum perforatum*). Although various degrees of success have been reported with regard to the treatment of insomnia using these various herbal treatments, there is no consensus regarding their use, recommended dosage, standardization of the preparation used or their effectiveness in relation to other, more standard stand-alone preparations. Furthermore, many plant-derived materials (including inter alia some of those listed above) have been shown to possess anti-inflammatory activity.

Several different formulations containing melatonin for use in the treatment of insomnia are known in the art. These formulations include inter alia oral dosage forms with either immediate-release or prolonged-release characteristics (liquids, capsules or tablets), sublingual dosage forms and transdermal patches. Administration of Immediate-release dosage forms generally lead to peak blood levels being obtained within about one hour. In the case of currently-available prolonged-release formulations, peak blood levels of melatonin are reached gradually over a period of 8-10 hours, thereby mimicking the body's internal secretion profile. The sublingual route for the delivery of pharmaceutical and nutraceutical agents, whereby the active ingredients are allowed to diffuse into the bloodstream through tissues under the tongue, is well known in the art. Many different classes of pharmaceutical agents have been formulated for sublingual administration, including: cardiovascular drugs, steroids, barbiturates, enzymes, and increasingly, vitamins and minerals. Various different dosage forms may be used for sublingual delivery, including sublingual tablets (regular or fast disintegrating), lipid matrix sublingual tablets, thin films and sublingual sprays.

There are several advantages associated with drug delivery by the sublingual route, in comparison with oral administration. Firstly, the direct entry of the medicament into the blood stream (i.e. via the capillaries located in the sub-epithelial connective tissue in the floor of the mouth), often leads to a shorter onset time. In addition, the more efficient uptake of the medicament may, in some cases, permit smaller dosages to be used. However, there is a further advantage of the sublingual route that is often even more significant. This advantage relates to the fact that since sublingually administered medicaments are not absorbed through the intestinal wall into the portal circulation, they are not subject to first-pass metabolism in the liver prior to entering the general circulation. Similarly, the drugs administered by this route are protected from the hostile gastrointestinal environment and thus are not degraded by stomach acid, bile and/or enzymes such as monoamine oxidase (MAO). This is a significant advantage, in particular for active ingredients that are metabolized by MAO, such as melatonin. In summary, it may be appreciated that administration via the sublingual route may often improve the bioavailability of the medicament. Many of the advantages described hereinabove are also features of other formulations from which the active ingredient is absorbed within the oral cavity, such as buccal formulations and chewable tablets.

Despite the many advantages discussed above, many of the known sublingual delivery systems suffer from the disadvantage that the delivery performance and the bioavailability of the active ingredient are affected by its physical properties, including solubility, crystal morphology, particle size, hygroscopicity, compressibility and polarity.

One of the aims of the present invention is to provide new and improved therapeutic compositions comprising melatonin, particularly suitable for use in the treatment of insomnia and/or inflammatory conditions.

Another aim is to provide melatonin-containing compositions which provide better onset/offset times, greater efficacy and reduced undesired effects (such as excessive morning sleepiness), when compared with prior art treatments.

A still further aim of the present invention is to provide compositions comprising synergistic combinations of melatonin and certain plant extracts.

Further aims and objectives will become apparent as the description proceeds.

SUMMARY OF THE PRESENT INVENTION

The present invention provides novel compositions comprising melatonin. These compositions are suitable for use inter alia in the treatment of a number of different conditions including, but not limited to, inflammatory conditions, anxiety and sleep disorders.

In some preferred embodiments the compositions of the present invention further comprise additional active agents including, but not limited to, natural material derived from a number of plant species including *Valeriana* species, *rosmarinus* species, *passiflora* species, and others, as well be described in detail hereinbelow.

In another aspect, the present invention is directed to novel dosage forms that are suitable for the administration of the presently-disclosed compositions. These dosage forms include ingestible oral formulations as well as sub-lingual dosage forms.

In a further aspect, the present invention encompasses methods of treating inflammatory disorders by means of administering a composition comprising a synergistic combination of melatonin, valerenic acid and carnosic acid.

In other embodiments, the present invention provides methods of treating anxiety and/or sleep disorders by means of administering a composition comprising melatonin, and optionally further comprising additional substances including, but not limited to, materials derived from *Valeriana* species, *rosmarinus* species, *passiflora* species, and others.

In a still further aspect, the present invention is directed to the use of the compositions disclosed hereinabove and described in detail hereinbelow in the preparation of medicaments. In some embodiments, these medicaments are suitable for the treatment of inflammatory disorders. In other embodiments, the medicaments are suitable for the treatment of anxiety and/or sleep disorders.

The present invention is further directed to compositions disclosed herein for the treatment of inflammatory disorders. In another embodiment, the invention is directed to compositions of the present invention for the treatment of anxiety and/or sleep disorders.

DETAILED DESCRIPTION OF PREFERRED EMBODIMENTS

Figure 1:
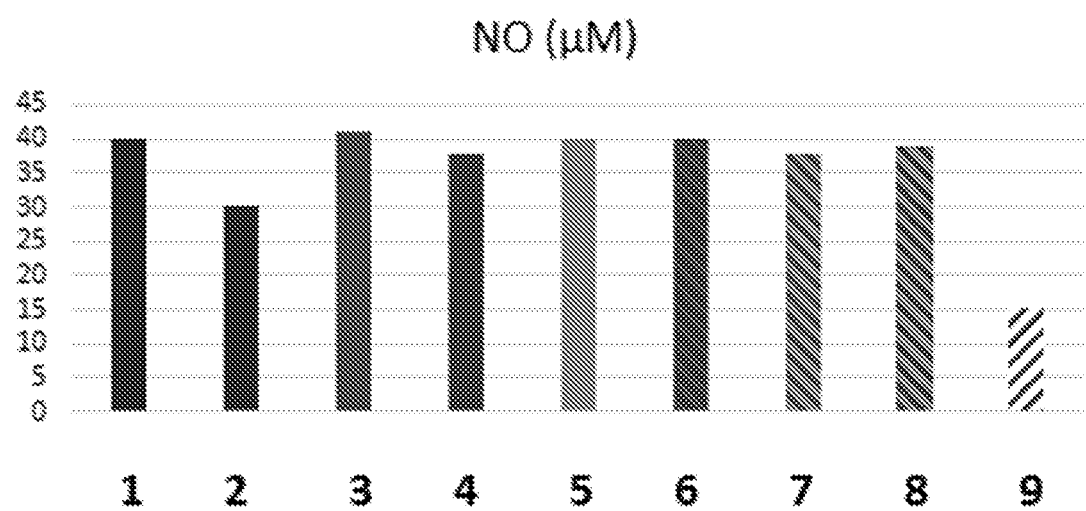
FIG. 1 presents results showing the synergistic interaction between melatonin, carnosic acid and valerenic acid in a murine cell model of nitric oxide release, wherein these components are present at a molar ratio of 1:1.4:2 (melatonin:carnosic acid:valerenic acid).
Figure 2:
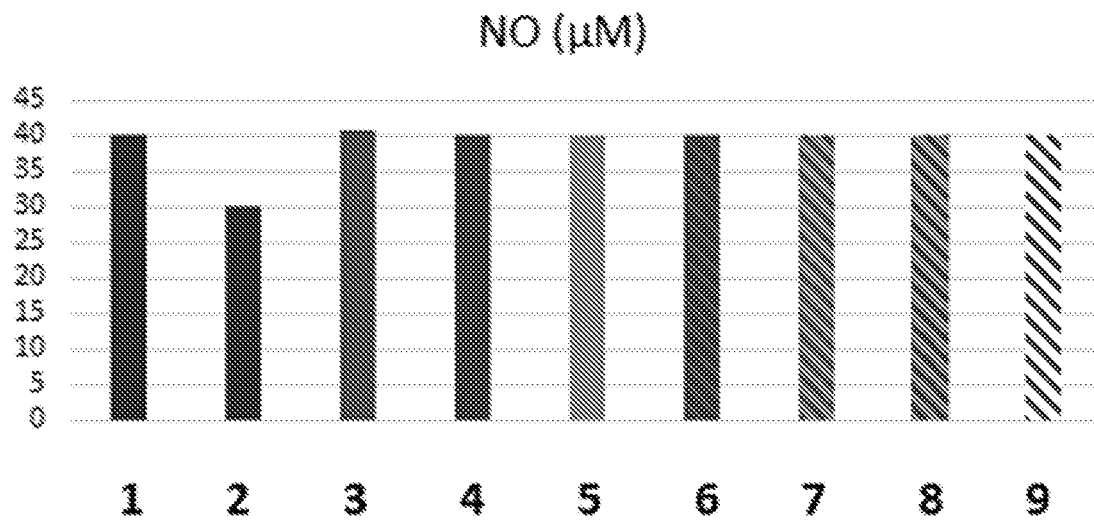
FIG. 2 presents results showing the absence of a synergistic interaction between melatonin, carnosic acid and valerenic acid in a murine cell model of nitric oxide release, when used at a molar ratio of 1:1.4:20 (melatonin:carnosic acid:valerenic acid).

As disclosed hereinabove, in one aspect the present invention is directed to compositions comprising melatonin as an active ingredient. Such compositions may be provided as pharmaceutical compositions, nutraceutical compositions, compositions for use in addition to food and beverage products, and so on.

In one particularly preferred embodiment of this aspect of the invention, the composition comprises a synergistic combination of melatonin, valerenic acid and carnosic acid. The latter two components may be present in synthetic form, as purified compounds obtained from natural plant material (*Valeriana* species and *Rosmarinus officinalis*, respectively), partially-purified extracts of said natural plant material, crude extracts of said plant material, and so on.

The term "synergistic combination", as used herein, refers to the fact that when combined together, the total biological activity of said combination is greater than the sum of the biological activities of each individual component of said combination when assayed individually, at the same concentrations as when combined. In particular, the present inventors have unexpectedly found that when used in combination, melatonin, valerenic acid and carnosic acid interact synergistically such that said combination possesses significantly greater anti-inflammatory activity than would be predicted from the anti-inflammatory activity of each of these agents when tested alone at the same concentration. The synergistic anti-inflammatory activity of this ternary (i.e. three-component) composition is demonstrated and compared with the activities of the binary combinations and individual agents (melatonin, valerenic acid and carnosic acid) in Working Examples 1-5, hereinbelow.

In one preferred embodiment of this aspect of the invention, the three obligatory active components of the composition are present in the following molar ratio ranges:

Melatonin:carnosic acid:valerenic acid
1:0.1-10:0.5-10

In another preferred embodiment, the three components are present in the following molar ratio ranges:

Melatonin:carnosic acid:valerenic acid
1:0.5-5:1-5

In one preferred embodiment, the three components are present in a molar ratio of:
Melatonin:carnosic acid:valerenic acid
1:0.7:1.3

In another preferred embodiment, the three components are present in a molar ratio of:
Melatonin:carnosic acid:valerenic acid
1:2.1:4

In a further preferred embodiment, the three components are present in a molar ratio of:
Melatonin:carnosic acid:valerenic acid
1:4:1

In another preferred embodiment, the three components are present in a molar ratio of:
Melatonin:carnosic acid:valerenic acid
1:1.5:2

The composition of this aspect of the present invention may optionally comprise further active ingredients, including, but not limited to plant-derived material, 5-hydroxytryptophan (5-HTP), tryptophan and other amino acids, vitamins and minerals.

In some preferred embodiments of this aspect of the invention, the additional active agents are plant-derived substances obtained from one or more of the following species:

Passiflora (*Passiflora incarnata*), chamomile (*Anthemis nobilis*), Hops (*Humulus lupulus*), lavender (*Lavandula officinalis*), wild lettuce (*Lactuca virosa*), california poppy (*Eschsholzia californica*), Kava kava (*Piper methysticum*), St. John's wort (*Hypericum perforatum*), rosemary (*Rosmarinus officinalis*) and the 5 HTP-containing plant *Griffonia simplicifolia*.

It is to be noted that the species listed above are given for the sake of illustration only, and other related species may also be used without deviating from the scope of the present invention.

In addition, the compositions of this aspect of the present invention may further comprise biologically inactive ingredients, including, but not limited to, one or more pharmaceutical excipients, such as binding agents, bulking agents, fillers, diluents, additional release-control polymers, polymeric matrices, disintegrants, flavorings, coating agents, penetration enhancers, and so on.

The compositions of this aspect of the present invention may be formulated in several different dosage forms for administration to mammalian (particularly human) subjects. Suitable dosage forms include (but are not limited to) oral dosage forms, sub-lingual dosage forms, injectable formulations, suppositories, patches for use on skin or mucous membranes, inhalable formulations, topical formulations and so on. Further details of the preparation of such formulations and dosage forms can be obtained from any standard reference on the subject, such as Remington's Pharmaceutical Sciences, Mack Publishing Co, Easton, Pa., USA, 21$^{st}$ edition (2006).

The details of a novel sublingual formulation that is suitable for the delivery of the synergistic composition of this aspect of the present invention are provided hereinbelow.

In some preferred embodiments of this aspect of the invention, the composition is formulated (e.g. as a sublingual tablet or swallowable tablet, caplet or capsule), such that each dosage unit (i.e. a single table, caplet or capsule) may comprise a combination of melatonin, carnosic acid and valerenic acid having amounts of each of the three main active components within the following preferred ranges:
Melatonin 0.2-5 mg
Carnosic Acid 2-5 mg
Valerenic Acid 1-5 mg In one particularly preferred embodiment, the amount of valerenic acid in each dosage unit is not less than 2 mg.

In another aspect, the present invention is directed to a method of treating and/or preventing inflammatory disorders in a mammalian (preferably human) subject, by means of administering a composition comprising a synergistic combination of melatonin, valerenic acid and carnosic acid (i.e. the composition disclosed in the previous section and described in more detail hereinbelow).

In one preferred embodiment of this method, the inflammatory condition to be prevented or treated may be one selected from the group consisting of acute inflammatory conditions, chronic inflammatory conditions, osteoarthritis rheumatoid arthritis, inflammatory conditions of the upper and lower respiratory tracts, peritonitis, cardiovascular inflammation, sepsis, trauma, inflammation of the skin (such as in psoriasis, acne, dermatitis and so on) and various types of gastrointestinal inflammation. This list is, of course, not exhaustive and is provided for exemplary purposes only.

In one preferred embodiment of this method of treatment and/or prevention of inflammatory conditions, the amounts of each of the three abovementioned active ingredients (melatonin, carnosic acid and valerenic acid) administered each day are:
Melatonin 0.3-4 mg/day
Carnosic acid 2-4 mg/day
Valerenic acid 3-5 mg/day In another aspect, the present invention is directed to a method of treating and/or preventing sleep disorders (such as insomnia) and/or anxiety in a mammalian (preferably human) subject, by means of administering a composition comprising a synergistic combination of melatonin, valerenic acid and carnosic acid (i.e. the composition disclosed in the previous section and described in more detail hereinbelow).

In a further aspect, the present invention is directed to the use of a composition comprising a synergistic combination of melatonin, valerenic acid and carnosic acid in the preparation of a medicament. In one preferred embodiment, the medicament is intended for use in the treatment and/or prevention of inflammatory disorders, as described hereinabove. In another preferred embodiment, the medicament is intended for use in the treatment and/or prevention of anxiety and/or sleep disorders (such as insomnia of different types). Suitable dosage forms, routes of administration and details of the synergistic combination are provided hereinabove.

In a still further aspect, the present invention is directed to a composition comprising a synergistic combination of melatonin, valerenic acid and carnosic acid for the treatment and/or prevention of inflammatory disorders (as described hereinabove).

In another aspect, the present invention is directed to a composition comprising a synergistic combination of melatonin, valerenic acid and carnosic acid for the treatment and/or prevention of anxiety and/or sleep disorders (such as insomnia).

In another aspect, the present invention provides a novel dosage form, which contains melatonin in a combination of both immediate release (IR) and controlled release (CR; also sometimes referred to as "extended release (ER)) forms. This combination when given sublingually (or in the form of buccal or chewable dosage forms) enables fast onset of the melatonin activity, together with prolonged activity that ensures a long-lasting therapeutic effect due to the controlled release component, which is capable of increasing the melatonin short half-life. In this way, the subject taking the dosage form is able to enjoy continuous undisturbed sleep. In addition, the combined IR/CR composition of the present invention also displays improved bioavailability and efficacy in relation to melatonin compositions of the prior art. A further advantageous feature of the presently-claimed composition is that when administered to a subject suffering from insomnia, it leads to both a rapid initial onset of sleep as well as a quick return to sleep after waking up mid-sleep.

It has also been unexpectedly found that when the above-disclosed melatonin dosage form further comprises certain plant-derived material from species such as *Valeriana officinalis, Rosmarinus officinalis*, and others, said plant-derived material interacts synergistically with the melatonin in enhancing its anti-insomnia and anxiolytic activities. It has also been found that these activities are further enhanced by adding additional substances such as *passiflora* extracts and whole plant material, other plant-derived material, green tea extracts, antioxidants and so on.

While these advantages of the present invention are seen when the melatonin IR/CR combination is formulated as a sublingual, buccal or chewable dosage form, other dosage forms, particularly oral dosage forms, containing this combination are also included within the scope of the present invention.

The present invention is thus primarily directed to a sublingual, buccal or chewable dosage form comprising a combination of melatonin IR and melatonin CR components, wherein said IR and CR components work synergistically to improve sleep quality. In addition, these combinations contain antioxidants that may have benefits in improving sleep quality and in some cases, such as with Vitamin E TPGS (d-alpha tocopheryl polyethylene glycol 1000 succinate), can serve as penetration enhancers as well.

Generally, each dosage form unit will contain about 1-10 mg of melatonin in the IR component and 1-10 mg of melatonin in the CR component.

In a highly-preferred embodiment, the dosage form further comprises vitamin E TPGS, which acts both as an anti-oxidant and as a penetration enhancer.

Preferably—but not exclusively—the dosage form of the present invention is formulated as a sublingual tablet. In one preferred embodiment, the sublingual tablet can be prepared as a double layer tablet where one part of the tablet dissolves and absorbed sublingually, while the ER components are swallowed and released continuously in the GI tract during the subsequent 1-12 hours.

In some preferred embodiments, the sublingual tablet can be prepared as a presscoat tablet, wherein the external layer contains melatonin in IR form, while the internal core contains melatonin in CR form.

In other preferred embodiments, the dosage form is formulated as a buccal tablet or chewable tablet.

The controlled release components of the dosage form may be prepared in accordance with any of the methods known to the skilled artisan in this field. Generally, in CR dosage forms the active pharmaceutical (or nutraceutical) ingredient is embedded within an insoluble matrix. The matrix is generally porous, and the active ingredient exits the matrix via the pores. In other types of CR formulation, the active ingredient is dissolved within a polymeric matrix which swells, thereby forming a gel through which said active ingredient needs to exit. In another approach, micro-encapsulation is used, whereby an inert core is coated with the active ingredient and then surrounded by one or more layers of insoluble envelope materials, the number, type and thickness of which may be selected in order to obtain the desired release characteristics. Many different types of controlled release polymer may be used to manufacture these various types of CR formulations, including (but not limited to): hydroxypropylmethyl cellulose, microcrystalline cellulose, methyl cellulose, hydroxypropyl cellulose, hydroxyethyl cellulose, sodium carboxymethyl cellulose, carboxymethyl ethyl cellulose, ethyl cellulose, and other cellulose derivatives, polymethacrylic copolymers, poloxamers, polyoxyethylene stearate, polyvinylpyrrolidone, polyvinylpyrrolidone-polyvinylacetate copolymers, polyvinyl alcohol, polyethylene oxide, and gums (e.g., xanthan gum or guar gum).

In one preferred embodiment of the present invention, the controlled release components of the dosage form are matrix minitabs, coated minitabs or coated microcapsules prepared by multistage layering or extrusion and spheronization followed by functional coating.

In addition to the two different forms of the active ingredient, melatonin, the dosage form of the present invention may further comprise one or more pharmaceutical excipients, including (but not limited to) binding agents, bulking agents, fillers, diluents, additional release-control polymers, polymeric matrices, disintegrants, flavors, coating agents, penetration enhancers, and so on.

In one preferred embodiment, the dosage form further comprises one or more penetration enhancers. Examples of two suitable penetration enhancers are menthol and vitamin E TPGS.

In another aspect, the present invention also encompasses a sublingual dosage form comprising a combination of melatonin IR and melatonin CR components. As disclosed hereinabove, said dosage form may further comprise one or more additional active insomnia-treating agents, wherein said agents are selected from the group consisting of plant-derived material, 5-hydroxytryptophan (5-HTP), tryptophan and other amino acids, vitamins and minerals.

In some preferred embodiments of this aspect of the invention, the additional active agents are plant-derived substances obtained from one or more of the following species:

valerian (*Valeriana officinalis*), passiflora (*Passiflora incarnata*), chamomile (*Anthemis nobilis*), Hops (*Humulus lupulus*), lavender (*Lavandula officinalis*), wild lettuce (*Lactuca virosa*), california poppy (*Eschsholzia californica*), Kava kava (*Piper methysticum*), St. John's wort (*Hypericum perforatum*), rosemary (*Rosmarinus officinalis*) and the 5 HTP-containing plant *Griffonia simplicifolia*.

It is to be noted that the species listed above are given for the sake of illustration only, and other related species may also be used without deviating from the scope of the present invention.

In one preferred embodiment, the present invention provides a sublingual dosage form comprising a combination of melatonin IR and melatonin CR components and material derived from *Valeriana officinalis* and/or other related *Valeriana* species. Preferably, the *Valeriana officinalis* material is present in the dosage form in an amount that contains in the range of about 1-10 mg valerenic acid.

In a further preferred embodiment, the present invention provides a sublingual dosage form comprising a combination of melatonin IR and melatonin CR components and material derived from *Valeriana officinalis* and/or other related *Valeriana* species, and material derived from *Rosmarinus officialis*. Preferably, the *Valeriana officinalis* material is present in the dosage form in an amount that contains in the range of about 1-10 mg valerenic acid.

In another preferred embodiment, the present invention provides a sublingual dosage form comprising a combination of melatonin IR and melatonin CR components and material derived from *Passiflora incarnata* and/or other related *Passiflora* species. Preferably, the *Passiflora incarnata* material is present in the dosage form in an amount in the range of about 10-300 mg.

In yet another preferred embodiment, the sublingual dosage form comprises a combination of melatonin IR and melatonin CR components, an extract of *Valeriana officinalis* containing 1-10 mg of valerenic acid, 10-100 mg of an extract of *Passiflora incarnata* and 10-100 mg of 5HTP.

It is to be noted that, as mentioned hereinabove, the plant-derived components of these dosage forms interact synergistically with melatonin, thereby enhancing its anti-insomnia activity.

It is to be noted that the term "plant-derived material" and similar expressions refer to material that is obtained in any of the various forms well known to the skilled artisan in this field, including: dried plant material obtained from roots, leaves, shoots, flowers and whole plants; aqueous and non-aqueous extracts; teas or tisanes; decoctions and tinctures; oils.

As explained hereinabove, sublingual tablets are the preferred type of formulation for the present invention. However, even though said tablets are intended for sublingual delivery (thereby providing rapid onset of activity), they may also be swallowed in the same way as standard oral dosage forms, when quick onset is not required.

In addition to the advantages of the dosage form of the present invention in relation to prior art melatonin preparations, it is to be noted that said dosage form also possesses improved efficacy with minimal side effects and residual tiredness, when compared with other anti-insomnia treatments of the prior art such as benzodiazepines.

It is to be noted that the above-disclosed dosage forms and compositions have also been found by the inventors to possess significant anxiolytic activity. Similarly, the addition of certain plant-derived (and other) agents, materials and substances to these compositions has now been found to cause synergistic enhancement of said anxiolytic activity. Without wishing to be bound by theory, it is believed that anxiety is often a significant factor in the development of insomnia and other sleep disorders. It is thus believed that the anxiolytic effect of the compositions of the present invention contribute (directly or indirectly) to the anti-insomnia effects of said compositions.

In another aspect, the present invention is directed to a method for treating insomnia in a human subject, wherein said method comprises the administration of a dosage form containing a combination of melatonin IR and melatonin CR components. Preferably, said dosage form is a sublingual tablet as disclosed and described hereinabove, and preferably, the administration of the dosage form is performed sublingually.

Similarly, the present invention also provides a method for improving sleep quality in a human subject, said method comprises the administration of a dosage form containing a combination of melatonin IR and melatonin CR components. Preferably, said dosage form is a sublingual tablet as disclosed and described hereinabove, and preferably, the administration of the dosage form is performed sublingually.

Furthermore, the present invention is also directed to a method for reducing anxiety in mammalian subjects (particularly human subjects), wherein said method comprises the administration of a dosage form containing a combination of melatonin IR and melatonin CR components. Preferably, said dosage form is a sublingual tablet as disclosed and described hereinabove, and preferably, the administration of the dosage form is performed sublingually.

In any of the methods of treatment defined above, the dosage form used may further comprise one or more further active ingredients such as plant-derived material, vitamins, minerals, 5-HTP, tryptophan and other amino acids, as described hereinabove.

EXAMPLES

In the following non-limiting examples, unless otherwise stated, the melatonin used was a synthetic melatonin obtained from Luotian Xinpusheng Pharmaceutica. Co. Ltd., Hubei, China. The valerian extracts were purchased from Indo World Trading Corp., Badarpur, India, while the *passiflora* extract was obtained from Bara Herbs, Yokneam, Israel. The rosemary extract was obtained from Vitiva, Markovci, Slovenia (product name Inolens 25). Other standard reagents and materials were purchased from several different laboratory and pharmaceutical suppliers.

WORKING EXAMPLES:
ANTI-INFLAMMATORY EFFECTS OF TESTED COMBINATIONS

Objectives

The objective of the studies reported in working examples 1-5 hereinbelow was to evaluate the anti-inflammatory properties of Melatonin, carnosic acid (Rosemary extract), Valerenic acid and combinations thereof on a cell line derived from murine macrophages (RAW 264.7 cells) activated by lipopolysaccharide (LPS).

General Methods:

$10^5$ RAW 264.7 cells were seeded in 96-well plates in a medium containing 1% FBS, 1% Glutamine and 1% Pen/strep in DMEM.

For dose response assays, cells were treated with 2-fold concentrations of Melatonin (starting from 15.6 µM up to 1000 µM LOT # XPS150311, Yes Pharma), Rosemary extract (0.1, 0.2, 0.4, 1, 2, 4, or 10 µM, Product #302659, Batch # LAB.16-659001, Vitiva) or 10% Valerenic acid (starting from 1.56 mg/ml up to 100 mg/ml, Batch # IWTC/5949/15001, Indo World Trading Corporation) for 6 hours. Then, the test solutions were removed and the cells were induced with lipopolysaccharide (LPS) (5 ng/ml). In addition, positive control cells were treated with 10 µM dexamethasone. Nitric oxide (NO) release was measured after incubation at 37° C., 5% $CO_2$ using a Griess Reagent System. The method is based on the chemical diazotization reaction that was originally described by Griess in 1879, which uses sulfanilamide and N-1-napthylethylenediamine dihydrochloride (NED) under acidic (phosphoric acid) conditions. This system detects $NO_2^-$ in a variety of biological and experimental liquid matrices such as tissue culture medium that was tested in this study.

For combination assays, cells were treated with various concentrations of Melatonin, Rosemary extract (containing 25% carnosic acid) and 10% Valerenic acid, at the final concentration indicated in each experiment, hereinbelow, for 22 hours together with LPS induction (5 ng/ml). The LPS concentration was chosen based on previous studies which showed no anti-inflammatory effect with the tested Items. In addition, positive control cells were treated with 10 μM dexamethasone. Nitric oxide (NO) release was tested after incubation at 37° C., 5% $CO_2$ using the Griess Reagent System.

Example 1

Anti-Inflammatory Effects of a Synergistic Combination of Melatonin, Carnosic Acid and Valerenic Acid All anti-inflammatory studies were performed using the techniques described in the 'General Methods' section, hereinabove.

To assess the anti-inflammatory effects of tested combinations in a preliminary study it was found that tested item should be incubated for 22 hours together with 5 ng/ml LPS.

The results from various treatments are summarized in FIG. 1 as follows: when tested separately none of the following individual components produced any significant inhibition of NO production when compared with the LPS-stimulated baseline cells (column 1): 0.5 μM Melatonin (column 3), 0.7 μM carnosic acid (column 4) and 1.3 μM valerenic acid (column 5). Similarly, the following binary combinations were also without effect on the level of NO production: 0.5 μM Melatonin and 0.7 μM carnosic acid (column 6); 0.5 μM Melatonin and 1.3 μM valerenic acid (column 7); 0.7 μM carnosic acid and 1.3 μM valerenic acid (column 8). However, the ternary combination of 0.5 μM Melatonin, 0.7 μM carnosic acid and 1.3 μM valerenic acid (column 9) caused marked inhibition of NO production by the cultured cells: 15 μM of NO instead of 40 μM in the LPS-stimulated, untreated cells (column 1). It is of interest to note that this inhibition is far greater than that caused by the dexamethasone positive control (30 μM; column 2).

The fact that none of the three components tested demonstrated any effect on this model when tested individually or even in binary combinations, indicates that there is a unexpected synergistic interaction between all three components when present together at the indicated relative molar ratio (0.5 μM Melatonin, 0.7 μM carnosic acid and 1.3 μM valerenic acid). Of particular interest is the fact that, at concentrations of the individual components which do not display an anti-inflammatory effect, the combination thereof at this ratio results in a significant inhibition of NO production.

Example 2

Absence of Anti-Inflammatory Effects of a Combination of Melatonin, Carnosic and Valerenic Acid when Valerenic Acid is Present at a High Concentration All anti-inflammatory studies were performed using the techniques described in the 'General Methods' section, hereinabove. This study was performed in the same general manner as described in Example 1, hereinabove. However, in this study, the relative amount of valerenic acid used was ten-times that used in Example 1.

The results from the various treatments are summarized in FIG. 1 as follows: when tested separately none of the following individual components produced any significant inhibition of NO production when compared with the LPS-stimulated baseline cells (column 1): 0.05 μM Melatonin (column 3), 0.07 μM carnosic acid (column 4) and 1.3 μM valerenic acid (column 5).

It may thus be concluded that the synergistic interaction between the three components tested is dependent on the relative amounts of each of said components when used in combination. In particular, a significantly elevated amount of valerenic acid appears to abolish the synergistic anti-inflammatory effect seen with the near-equimolar combination (as shown in Example 1).

WORKING EXAMPLES: ANXIOLYTIC EFFECTS OF TESTED COMBINATIONS

Example 3

Synergistic Interaction Between Melatonin and Valerian: Anxiolytic Effect

Open field tests were used as a measure of the spontaneous activity of laboratory rats, in order to measure the anxiolytic effects of melatonin, valerian and a combination of these two substances.

Method:

Rats were placed in a behavioral room one hour before testing procedures, for purpose of habituation.

Activity was tested in open boxes (open-fields: 80 cm wide, 80 cm large, 60 cm high) made of transparent Plexiglas. Animals were individually placed in the open-fields for 15 minute sessions. The following parameters were recorded: Indices of motor exploratory activity: the distance traveled, mobility time, Open Field spontaneous activity is performed on the testing day, 30 minutes after the administration of a test substance (melatonin, valerian, a combination of the two, or vehicle).

Indices of habituation: distance traveled.
  During the last 5 minute period in percent of the first as last 5 minute periods.

Indices of anxiety:
  Percentage of distance traveled in the central zone of the open-field.
  Percentage of time spent in the central zone of the open-field.

Figure 3:
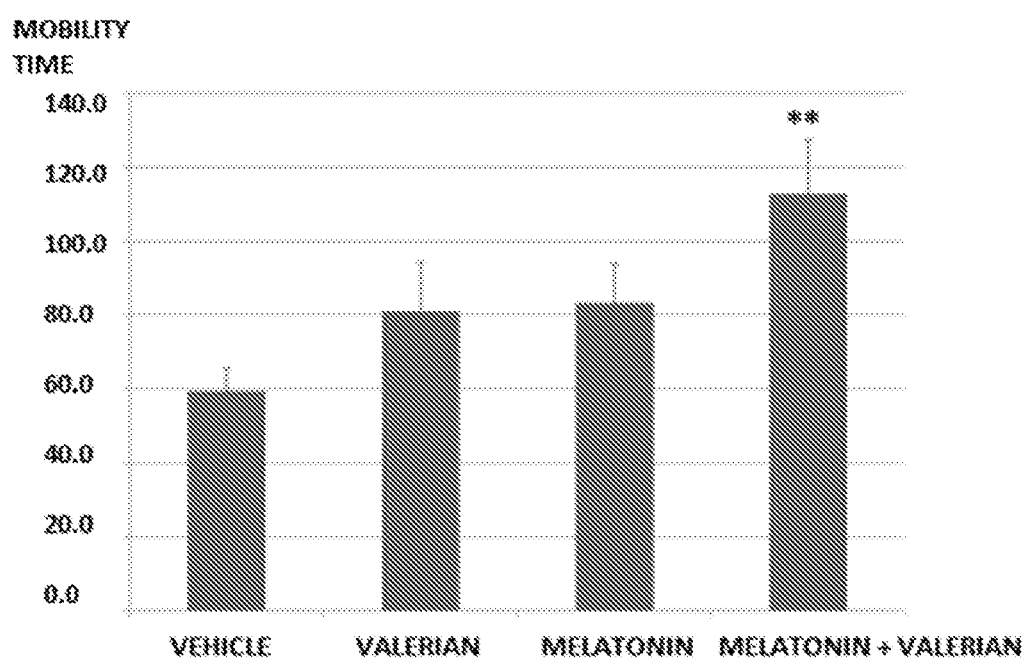
FIG. 3 presents results obtained from a laboratory rat spontaneous activity model, in which a synergistic anxiolytic interaction between melatonin and valerian is observed.

Results:

The effect of the test substances are shown in the bar graph presented in FIG. 3. It may be seen from this graph that both melatonin and valerian (when administered separately) increased the mobility time of the rats (in comparison to the vehicle control), indicating they both possess anxiolytic effects. However, the difference in mobility time between test substance and vehicle control only reached statistical significance when melatonin was administered in combination with valerian (last bar in FIG. 3).

These results are highly suggestive of a synergistic interaction between melatonin and valerian with respect to their anxiolytic activity.

Example 4

Synergistic Interaction Between Melatonin and Valerian: Base-Line and Caffeine-Induced Anxiolytic Effect As in Example 3, above, open field tests were used to measure the anxiolytic effects of melatonin, valerian and a combination of these two substances. However, in some of the rats in the present study, the effect of the test substances was measured in rats which had also received caffeine. Thus, while the study reported in Example 3 provided insights into the effect of melatonin and valerian on base-line anxiety, the results obtained in this study relate to the effect of these substances on both base-line and caffeine-induced ("caffeine-relaxed") subjects.

Method:

The same open-field method was used as in Example 3. However, in this study, the parameter that was measured was the "center time" that is, the time that the rats spend in the center of tested arena. The center time was used as an index for the anxiolytic effect of the test substances in both "base-line" and "caffeine-relaxed" rats.

Figure 4:
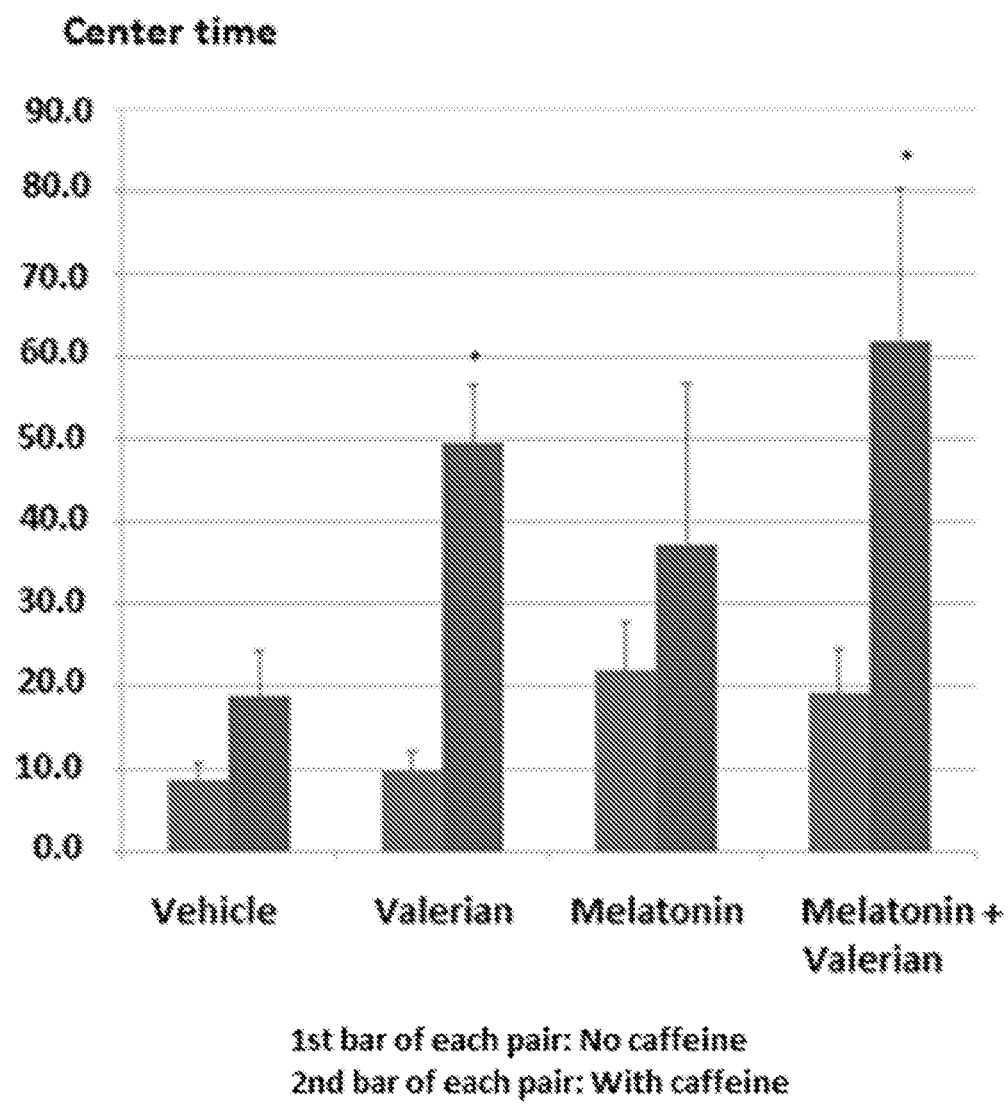
FIG. 4 presents results indicating a synergistic interaction between melatonin and valerian as measured by changes in the 'center time' observed in an open-field rat anxiety model.

Results:

The effect of the test substances is shown in FIG. 4. It may be seen from this graph that in the "base-line" animals (i.e. those that had not received caffeine; left-hand bar of each pair of bars), both melatonin and valerian (when administered separately) increased the mobility time of the rats (in comparison to the vehicle control), indicating they both possess anxiolytic effects. However, in the case of the caffeine-relaxed rats (right-hand bar of each pair of bars), only valerian (both when used separately and when combined with melatonin) affected caffeine induced center motility.

These results suggest that melatonin may operate as an anxiolytic and hypnotic agent via different receptors and pharmacological mechanisms than those used by valerian, and that these two substances interact synergistically when used in combination.

PREPARATIVE EXAMPLES

Example 5

Preparation of Controlled Release Melatonin Minitabs

1. Dissolve 12 g melatonin together with 12 g Vitamin E TPGS, 8 g polyvinylpyrrolidone (PVP K25) in 150 g absolute ethanol.
2. Mix together 40 g Hydroxypropylmethyl cellulose (HPMC K15M), 24 g HPMC E50, 20 g Kucel® LF, 40 g Avicel® pH 101.
3. Add the melatonin solution from stage 1 and granulate in high shear granulator for 1 minute.
4. Dry the wet granulate in Glatt fluid bed dryer, inlet temperature 60 degrees C. for 45 minutes.
5. Sieve the dry granules through a 0.8 mm sieve.
6. Add 2 g aerosol and mix for 5 minutes. Add 1 g magnesium stearate and mix for 1 minute.
7. Compress the granules into 2 mm controlled release minitabs.

Example 6

Preparation of Sublingual Tablets Containing Immediate and Slow Release Melatonin 1. Dissolve in 100 g ethanol: 2.9 g melatonin, 9.6 g Vitamin E TPGS, 19.2 g PVP K25.
2. Mix together: 108 g lactose, 204 g mannitol.
3. Add the granulation solution from stage 1 and granulate for 1 minute in high shear granulator, Diosna 1 type.
4. Dry the wet granulate in a fluid bed dryer for 45 minutes with an inlet temperature of 60 degrees C.
5. Screen through a 0.8 mm sieve.
6. Add to the sieved mixture: 24 g of the controlled release minitabs prepared in Example 5, 19 g *stevia* sweetener, 24 g starch 1500 (pregelatinized), 5.6 g menthol crystals, 3.8 g aerosol 200. Mix 10 minutes.
7. Add 1.9 g magnesium stearate and mix for 3 minutes.
8. Compress the mixture into sublingual tablets, each containing about 3 mg melatonin immediate release and 3 mg controlled release melatonin.

Example 7

Preparation of Sublingual Tablets Containing Immediate and Slow Release Melatonin and Valerian Extract 1. Dissolve in 100 g ethanol: 2.9 g melatonin, 3.8 g valerenic acid (38 g valerian extract, 10% valerenic acid), 9.6 g Vitamin E TPGS and 19.2 g PVP K25.
2. Mix together: 108 g lactose and 200 g mannitol.
3. Add the granulation solution from stage 1 and granulate for 1 minute in a high shear granulator, Diosna 1 type.
4. Dry the wet granulate in a fluid bed dryer for 45 minutes with an inlet temperature of 60 degrees C.
5. Screen through a 0.8 mm sieve.
6. Add to the sieved mixture: 24 g of the controlled release minitabs prepared in Example 5, 19 g *stevia* sweetener, 24 g starch 1500 (pregelatinized), 5.6 g menthol crystals and 3.8 g aerosol 200. Mix for 10 minutes.
7. Add 1.9 g magnesium stearate and mix for 3 minutes.
8. Compress the mixture into sublingual tablets each containing about 3 mg melatonin immediate release, 4 mg valerenic acid and 3 mg controlled release melatonin.
9. The tablets are further coated with Sepifilm LP 770 humidity protecting coating.

Example 8

Preparation of Sublingual Tablets Containing Immediate and Slow Release Melatonin, Rosemary Extract and Valerian Extract 1. Dissolve in 100 g ethanol: 2.9 g melatonin, 3.8 g valerenic acid (38 g valerian extract, 10% valerenic acid), 9.6 g Vitamin E TPGS and 19.2 g PVP K25.
2. Mix together: 108 g lactose, 12 gr rosemary extract powder (25% carnosic acid) and 200 g mannitol.
3. Add the granulation solution from stage 1 and granulate for 1 minute in a high shear granulator, Diosna 1 type.
4. Dry the wet granulate in a fluid bed dryer for 45 minutes with an inlet temperature of 60 degrees C.
5. Screen through a 0.8 mm sieve.
6. Add to the sieved mixture: 24 g of the controlled release minitabs prepared in Example 5, 19 g *stevia* sweetener, 24 g starch 1500 (pregelatinized), 5.6 g menthol crystals and 3.8 g aerosol 200. Mix for 10 minutes.
7. Add 1.9 g magnesium stearate and mix for 3 minutes.
8. Compress the mixture into sublingual tablets each containing about 3 mg melatonin immediate release, 4 mg valerenic acid and 3 mg controlled release melatonin.
9. The tablets are further coated with Sepifilm LP 770 humidity protecting coating.

Example 9

Preparation of Sublingual Tablets Containing Immediate and Slow Release Melatonin and *Passiflora* Extract 1. Dissolve in 100 g ethanol: 2.9 g melatonin, 9.6 g Vitamin E TPGS and 19.2 g PVP K25.

2. Mix together: 108 g lactose, 104 g mannitol and 100 g *Passiflora incarnate* extract.

3. Add the granulation solution from stage 1 and granulate for 1 minute in a high shear granulator, Diosna 1 type.

4. Dry the wet granulate in a fluid bed dryer for 45 minutes with an inlet temperature of 60 degrees C.

5. Screen through a 0.8 mm sieve.

6. Add to the sieved mixture: 24 g of the controlled release minitabs prepared in Example 5, 19 g *stevia* sweetener, 24 g starch 1500 (pregelatinized), 5.6 g menthol crystals and 3.8 g aerosol 200. Mix for 10 minutes.

7. Add 1.9 g magnesium stearate and mix for 3 minutes.

8. Compress the mixture into sublingual tablets each containing about 3 mg melatonin immediate release, 100 mg *Passiflora incarnate* and 3 mg controlled release melatonin.

The invention claimed is:

1. A composition comprising a synergistic combination of melatonin, valerenic acid and carnosic acid.

2. The composition according to claim 1, wherein the melatonin, valerenic acid and carnosic acid are present in a molar ratio of:
Melatonin:Carnosic acid:Valerenic acid
1:0.1-10:0.5-10.

3. The composition according to claim 1, wherein the melatonin, valerenic acid and carnosic acid are present in a molar ratio of:
Melatonin:Carnosic acid:Valerenic acid
1:0.5-5: 1-5.

4. The composition according to claim 1, where the melatonin, valerenic acid and carnosic acid are present in a molar ratio of:
Melatonin:carnosic acid:valerenic acid
1:1.5:2.

5. The composition according to claim 1, wherein the melatonin, valerenic and carnosic acid are each provided in a form selected from the group consisting of synthetic compounds, purified compounds obtained from plant material, partially purified extracts of plant material and crude extracts of plant material.

6. A method for treating and/or preventing inflammatory disorders in a mammalian subject, comprising administering a composition according to claim 1.

7. The methods according to claim 6, wherein the mammalian subject is a human subject.

8. A method for treating and/or preventing sleep disorders in a mammalian subject, comprising administering a composition according to claim 1.

9. A method for treating and/or preventing anxiety in a mammalian subject, comprising administering a composition according to claim 1.

10. A method comprising preparing a medicament including a composition according to claim 1.

11. The method according to claim 10, further comprising administering the medicament for treatment and/or prevention of inflammatory disorders.

12. The method according to claim 10, further comprising administering the medicament for treatment and/or prevention of sleep disorders.

13. The method according to claim 10, further comprising administering the medicament for treatment and/or prevention of anxiety.

* * * * *